US007131837B2

(12) United States Patent
Guaragno et al.

(10) Patent No.: US 7,131,837 B2
(45) Date of Patent: Nov. 7, 2006

(54) VERTICALLY AND HORIZONTALLY STANDING DENTAL SCALER SYSTEM AND METHOD

(75) Inventors: Kenneth R. Guaragno, Spring Grove, PA (US); Eric Ursprung, Camp Hill, PA (US)

(73) Assignee: Dentsply International Inc., York, PA (US)

( * ) Notice: Subject to any disclaimer, the term of this patent is extended or adjusted under 35 U.S.C. 154(b) by 200 days.

(21) Appl. No.: 10/698,113

(22) Filed: Oct. 31, 2003

(65) Prior Publication Data

US 2005/0095555 A1 May 5, 2005

(51) Int. Cl.
*A61C 13/38* (2006.01)
(52) U.S. Cl. .................................. 433/77; 433/119
(58) Field of Classification Search .............. 433/77, 433/78, 79, 119, 28, 49; 132/310
See application file for complete search history.

(56) References Cited

U.S. PATENT DOCUMENTS

| 3,645,255 A | 2/1972 | Robinson ............... 128/24 A |
| 3,703,037 A | 11/1972 | Robinson ................... 32/58 |
| 4,019,254 A | 4/1977 | Malmin ..................... 32/57 |
| 4,051,337 A | 9/1977 | Warrin ................. 200/61.85 |
| 4,080,737 A | 3/1978 | Fleer ......................... 32/22 |
| 4,110,908 A | 9/1978 | Cranston ................... 32/50 |
| 4,253,831 A | 3/1981 | Eaton, II .................. 433/91 |
| 4,375,964 A | 3/1983 | Knopp et al. ............. 433/29 |
| 4,492,574 A | 1/1985 | Warrin et al. ............. 433/81 |
| 4,501,355 A * | 2/1985 | Hoffman ................ 206/77.1 |
| 4,682,949 A | 7/1987 | Warrin ...................... 433/81 |
| 4,818,229 A | 4/1989 | Vasile ..................... 433/127 |
| 4,820,152 A | 4/1989 | Warrin et al. ............. 433/86 |
| 4,979,899 A | 12/1990 | Römhild et al. .......... 433/121 |
| 5,127,830 A * | 7/1992 | Sheridan et al. ........... 433/77 |
| 5,158,455 A | 10/1992 | Bailey ....................... 433/88 |
| 5,236,358 A | 8/1993 | Sieffert ................... 433/119 |
| 5,302,123 A | 4/1994 | Bechard .................. 433/104 |
| 5,382,162 A | 1/1995 | Sharp ...................... 433/116 |

(Continued)

FOREIGN PATENT DOCUMENTS

EP    0 125 784    11/1984

(Continued)

OTHER PUBLICATIONS

"New Seagate External Hard Drive Is Easiest, Most Rugged, And Coolest On the Market." Sep. 24, 2003. www.seagate.com.*

*Primary Examiner*—Chris L. Rodriguez
*Assistant Examiner*—Patrick J. Kilkenny
(74) *Attorney, Agent, or Firm*—Daniel W. Sullivan; James B. Bieber; Douglas J. Hura

(57) ABSTRACT

The invention provides a dental scaler system and method of use. The dental scaler system has a dental scaler apparatus and a scaler handpiece enclosing a coil. The dental scaler apparatus has a housing and a scaler power control circuit. The coil is connected through an electrical conductor to the scaler power control circuit. The housing has a holder side, and a first and a second base side each having a plurality of first base feet extending therefrom. The first base side is connected to the second base side at an angle greater than 30 degrees. The second base side is connected to the holder side. The holder side has a scaler handpiece holder integrally formed therein. In the method the system is supported on the first feet, and then on the second feet.

8 Claims, 6 Drawing Sheets

U.S. PATENT DOCUMENTS

| | | | |
|---|---|---|---|
| 5,395,240 A | 3/1995 | Paschke et al. | 433/119 |
| 5,451,161 A | 9/1995 | Sharp | 433/119 |
| 5,480,302 A | 1/1996 | Fife | 433/116 |
| 5,501,596 A | 3/1996 | Bailey | 433/86 |
| 5,730,594 A | 3/1998 | Sharp | 433/119 |
| 5,927,977 A | 7/1999 | Sale et al. | 433/86 |
| 6,062,858 A | 5/2000 | Hugo et al. | 433/119 |
| 6,086,369 A | 7/2000 | Sharp et al. | 433/118 |
| 6,164,968 A | 12/2000 | Feine | 433/119 |
| 6,190,167 B1 | 2/2001 | Sharp | 433/119 |
| 6,293,793 B1 | 9/2001 | Schuman et al. | 433/86 |
| 6,450,811 B1 * | 9/2002 | Pollock et al. | 433/86 |

FOREIGN PATENT DOCUMENTS

| | | |
|---|---|---|
| EP | 0 158 136 | 10/1985 |
| EP | 0 294 548 | 12/1988 |
| EP | 0 305 357 | 3/1989 |
| EP | 0 454 188 | 10/1991 |
| EP | 0 293 654 | 3/1992 |
| EP | 0 898 941 | 3/1999 |
| JP | 6-261918 | 9/1994 |
| JP | 7-100154 | 4/1995 |
| JP | 8-173454 | 7/1996 |
| JP | 9-10227 | 1/1997 |
| JP | 10-14948 | 1/1998 |
| JP | 10-61642 | 3/1998 |
| JP | 2003248526 A * | 9/2003 |
| WO | 95/15127 | 6/1995 |
| WO | 96/00631 | 1/1996 |
| WO | 98/12980 | 4/1998 |
| WO | 98/23222 | 6/1998 |
| WO | 99/60943 | 12/1999 |
| WO | 01/12095 A1 | 2/2001 |
| WO | 01/45581 A1 | 6/2001 |

* cited by examiner

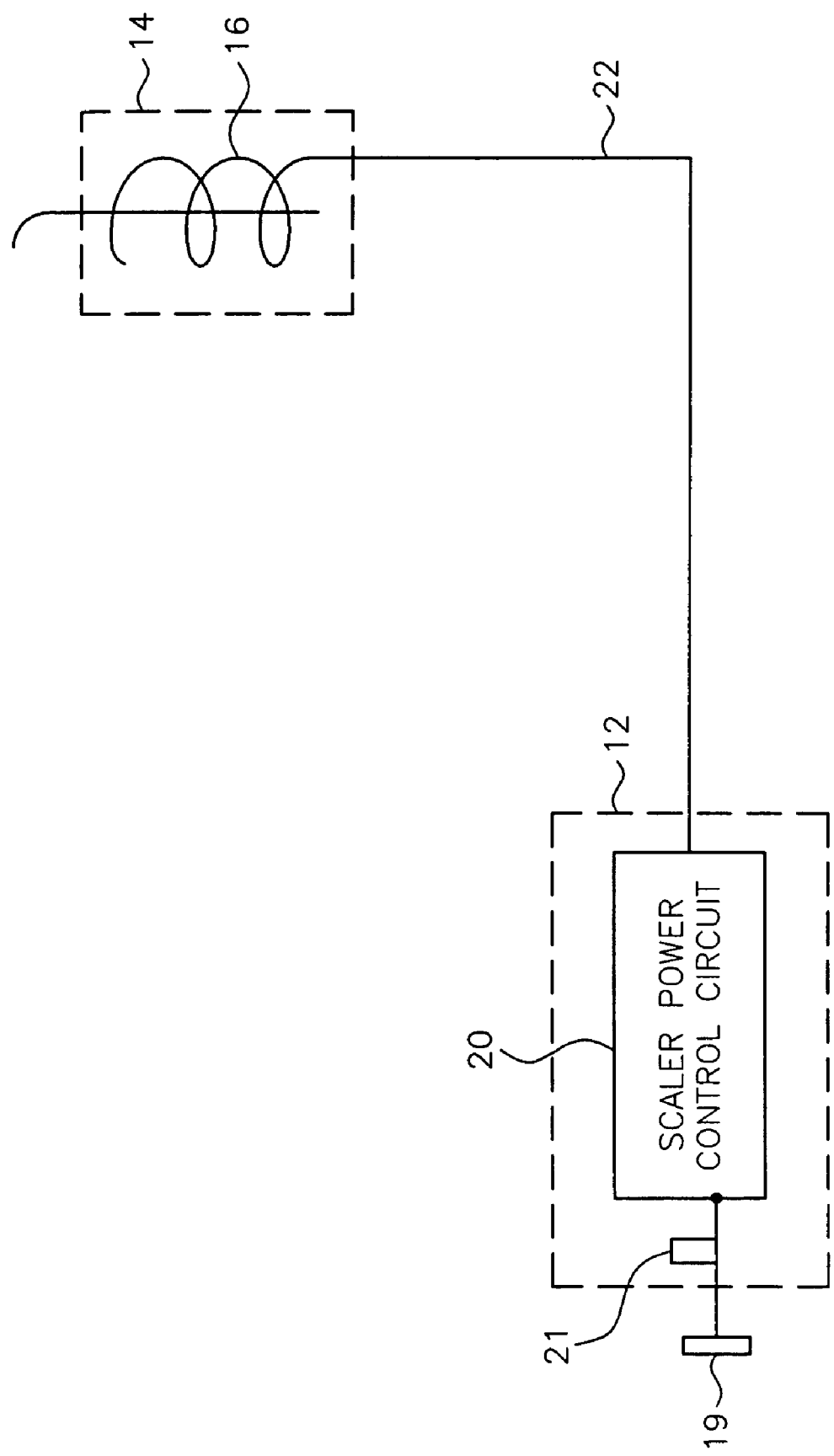

VERTICALLY AND HORIZONTALLY STANDING DENTAL SCALER SYSTEM AND METHOD

BACKGROUND OF INVENTION

Field of the Invention

The present invention relates generally to an electronically controlled dental scaler system and method. More particularly, the dental scaler system includes an apparatus that can be placed in a vertical or horizontal standing position.

SUMMARY OF THE INVENTION

The present invention provides a dental sealer apparatus having a power control circuit. A scaler handpiece is attached to the apparatus by a handpiece connector cable. The sealer housing includes a first base side having a plurality of first base feet extending therefrom. The first base feet substantially support the housing when it is standing in a vertical position. The scaler housing also includes a second base side, which is integrally connected to the first base side, having a plurality of second base feet extending therefrom. The second base feet substantially support the housing when it is standing in a horizontal position. The apparatus also includes a holder side, which is integrally connected to the second base side, and includes a handpiece holder for supporting the scaler handpiece when the handpiece is not being used. In addition, the apparatus includes an integrally connected control side with at least one adjuster knob.

BRIEF DESCRIPTION OF THE DRAWINGS

FIG. 6 is a schematic diagram of the circuit of the dental scaler system of FIGS. 1 THROUGH 5.

DESCRIPTION OF THE INVENTION

Figure 1:
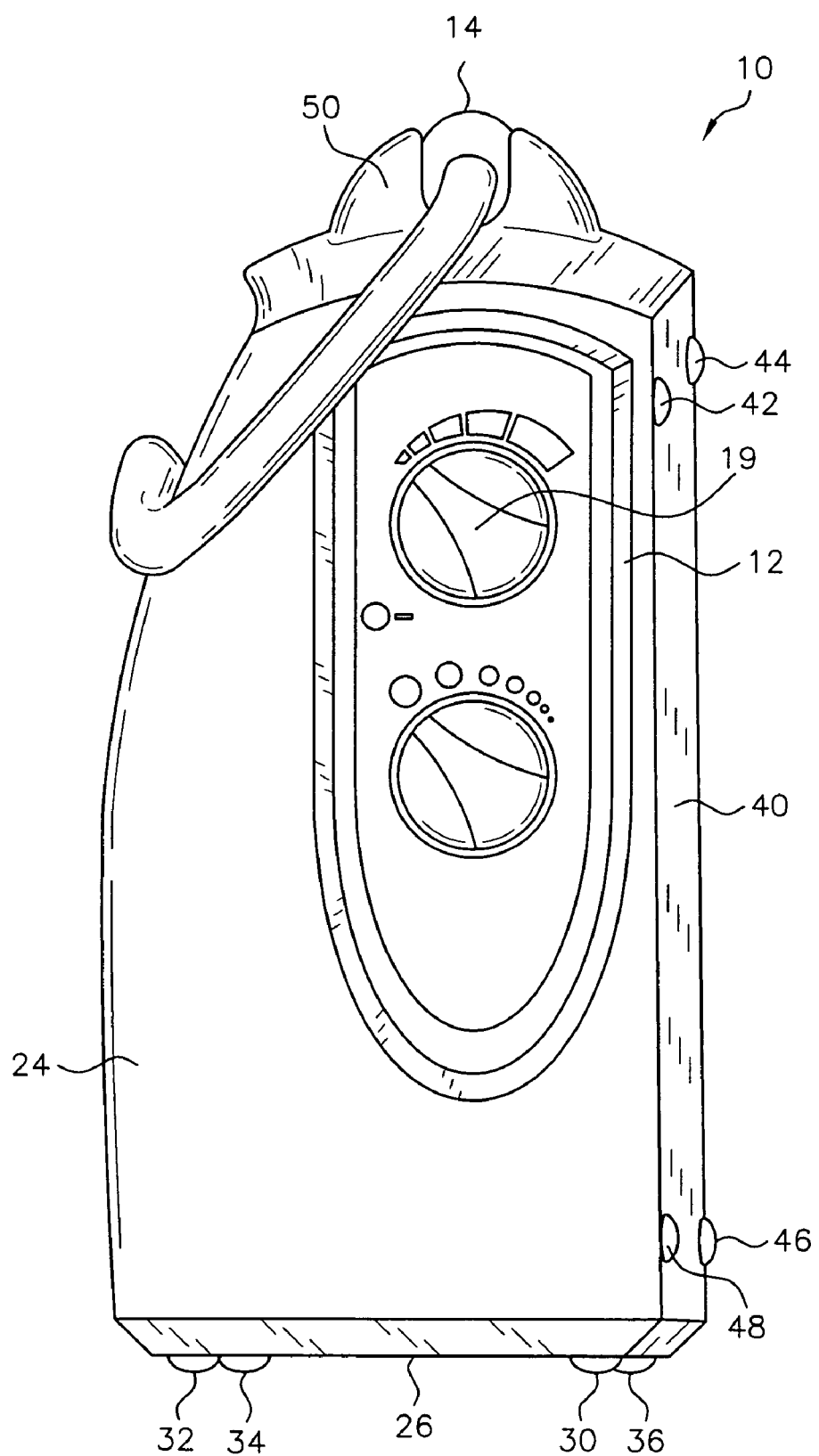
FIG. 1 is a frontal perspective view of a dental scaler system in accordance will, the invention with the housing in its vertical position.
Figure 2:
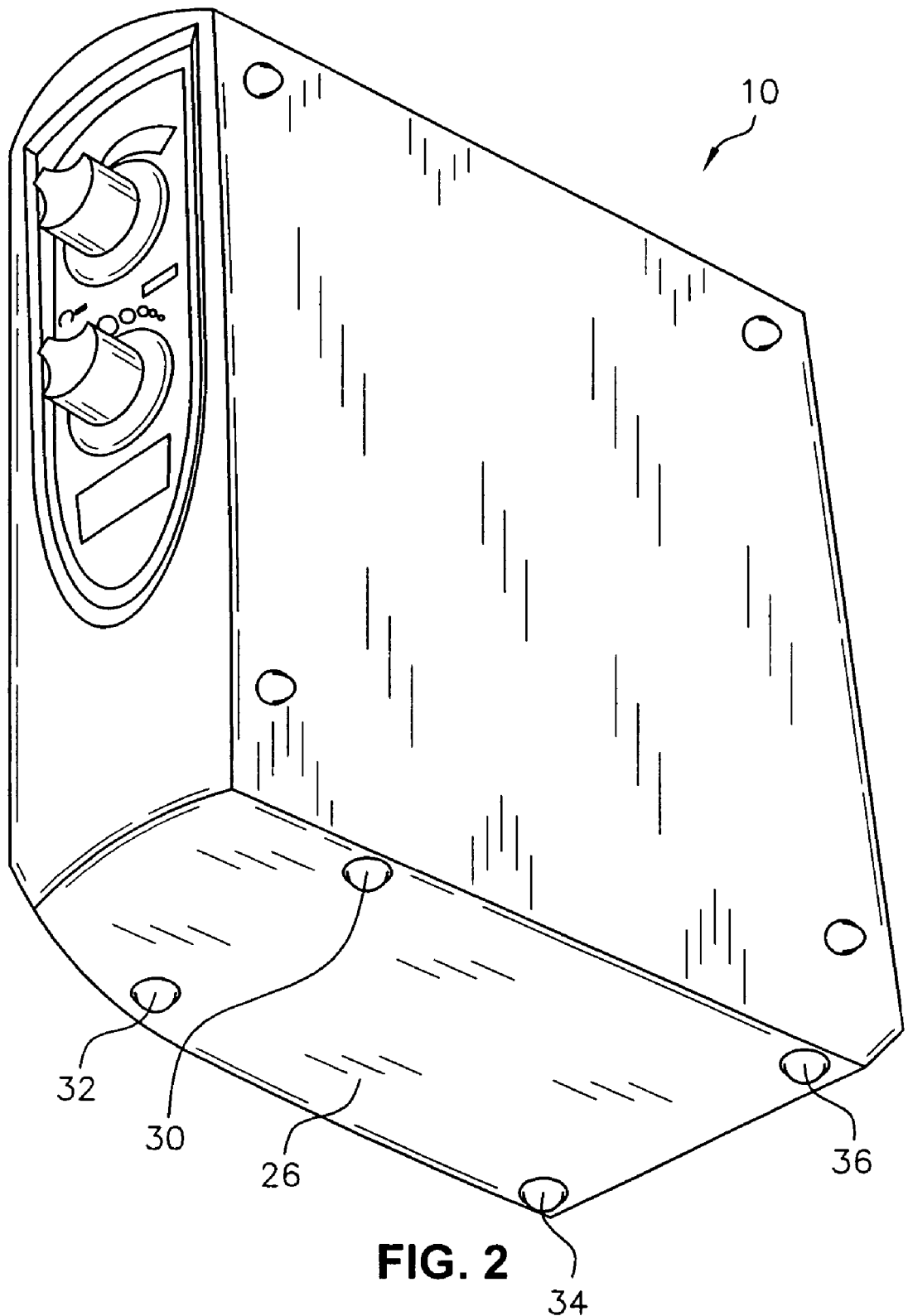
FIG. 2 is a side perspective view of a dental scaler system in accordance with the invention with the housing in its vertical position.
Figure 3:
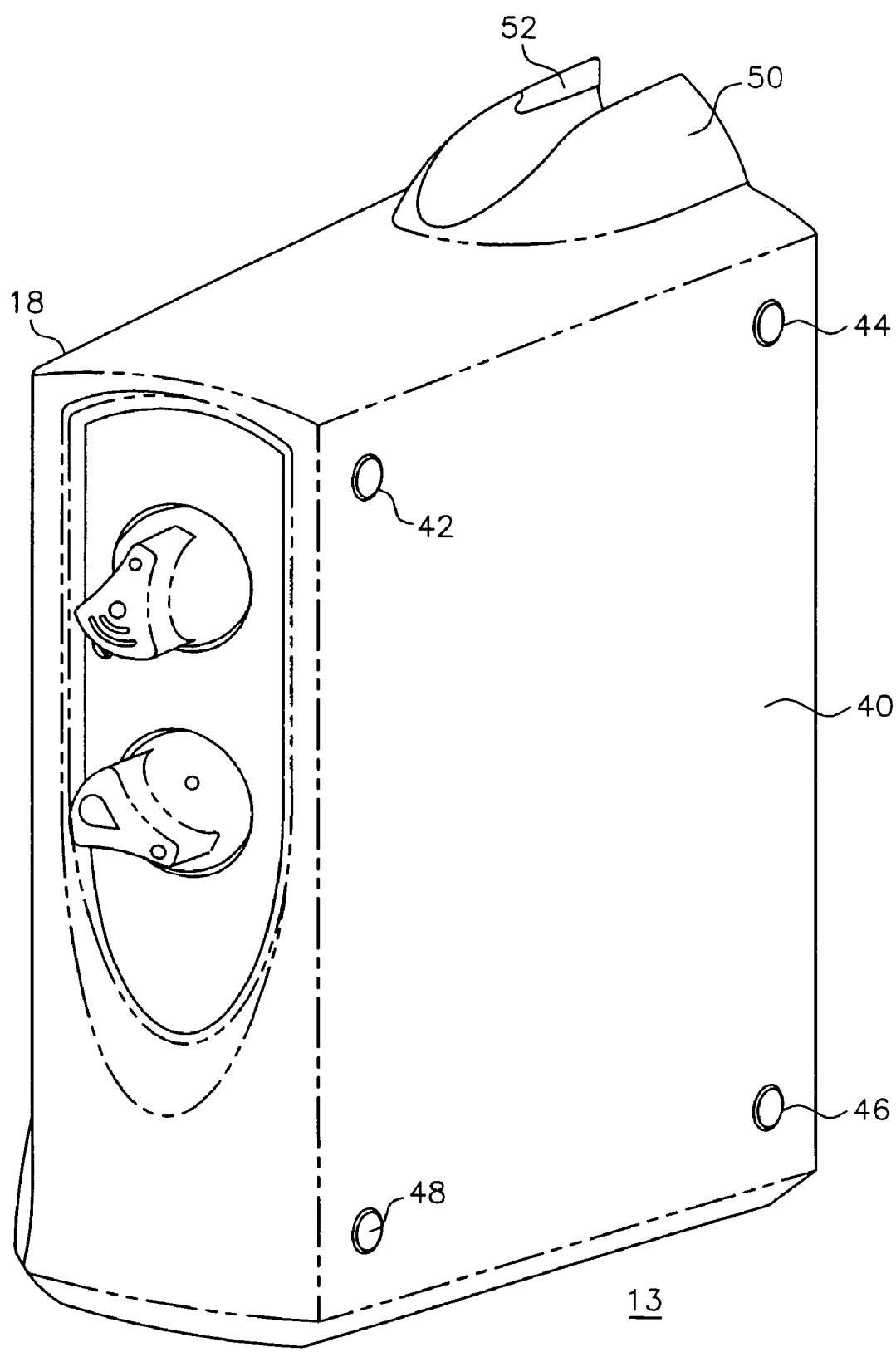
FIG. 3 is a side perspective view of the housing in its vertical position as shown in FIG. 2.
Figure 4:
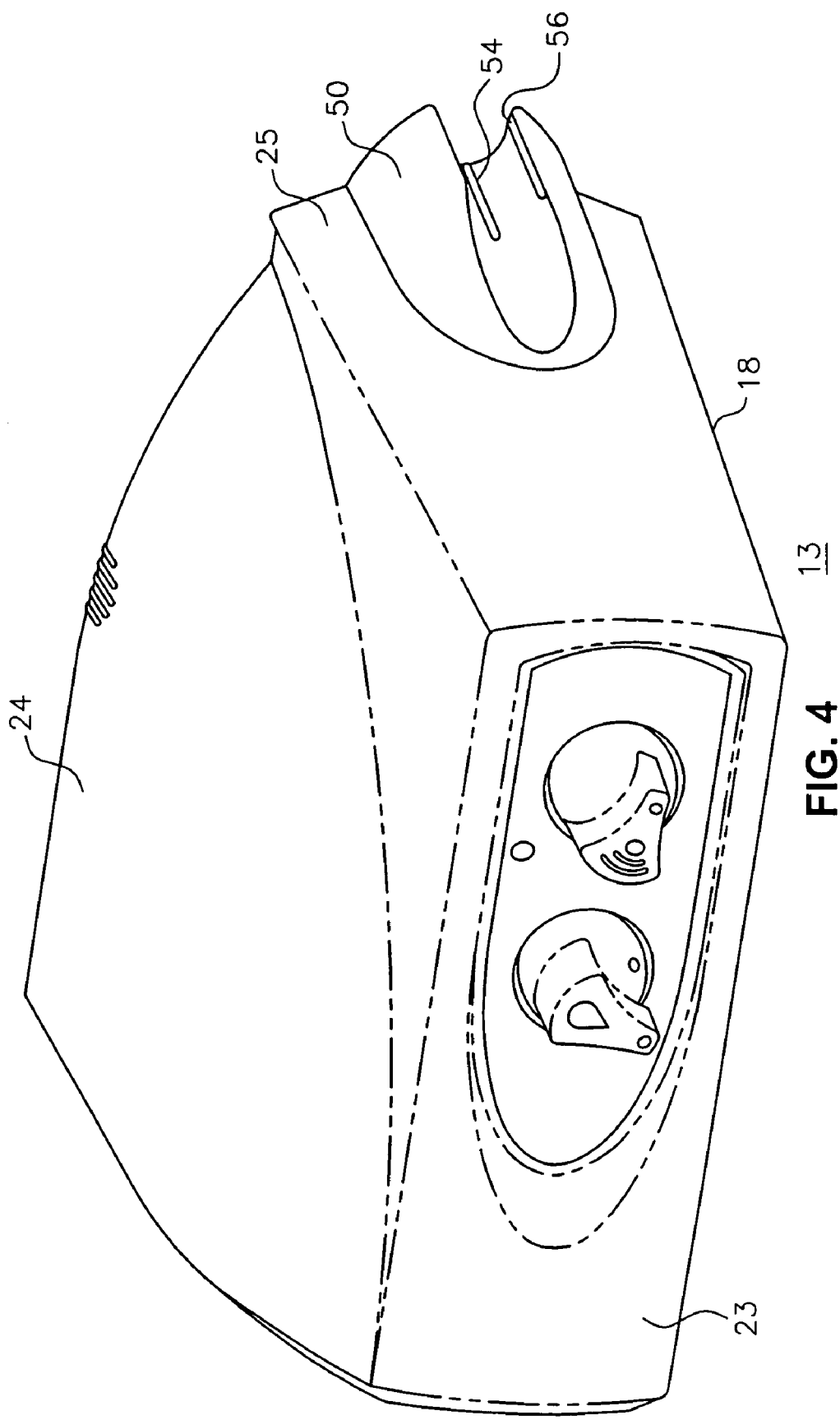
FIG. 4 is a frontal perspective view of the housing in its horizontal position.
Figure 5:
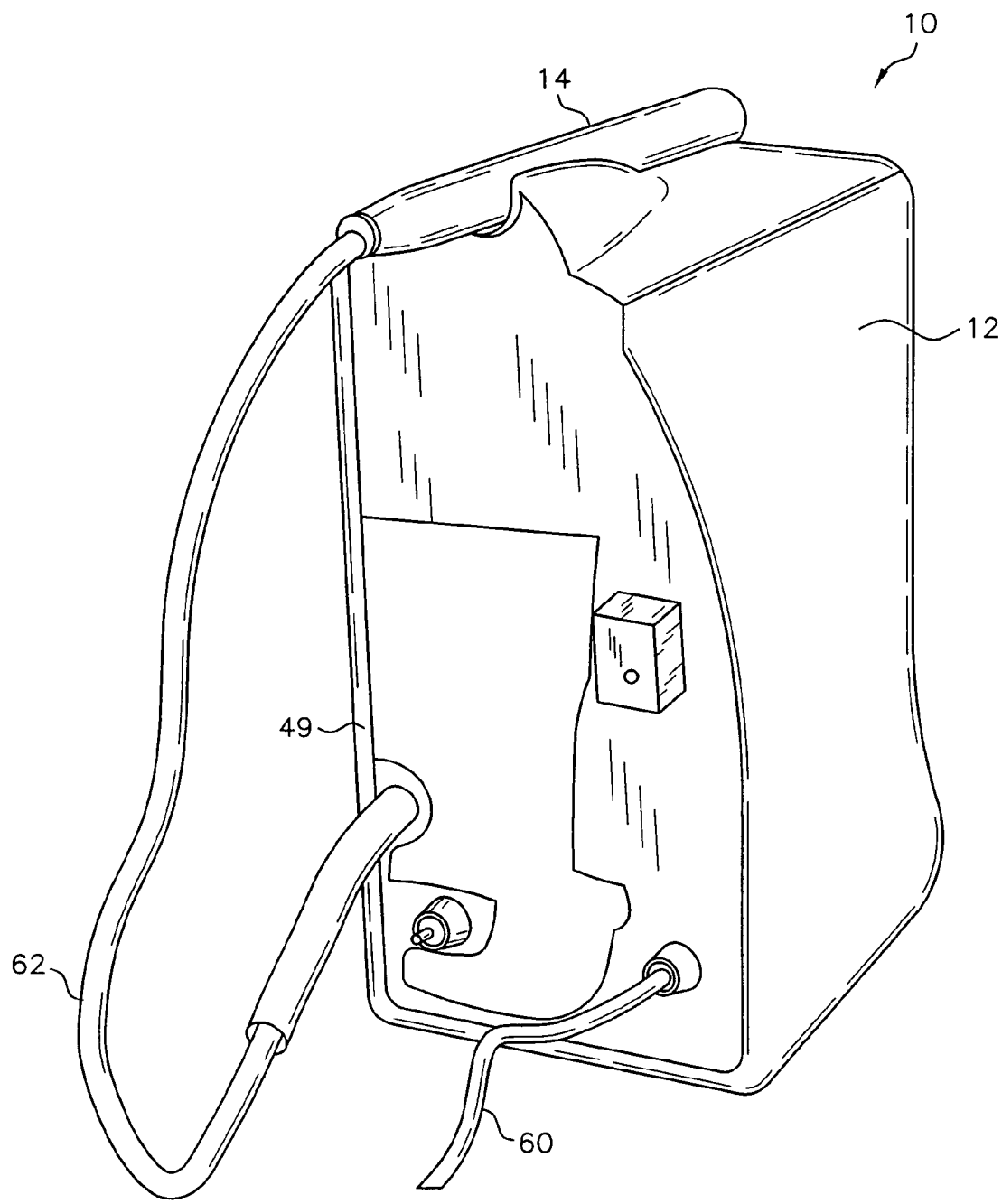
FIG. 5 is a rear perspective view of the housing.

The invention is now described with more particular reference to FIGS. 1 through 6. With more particular reference to FIG. 1 is seen dental scaler system 10 having dental scaler apparatus 12 and scaler handpiece 14 having coil 16. Scaler handpiece 14 has tip (not shown) and magnetostrietive stack (not shown). Dental scaler apparatus 12 has housing 18 and scaler power control circuit 20. Dental scaler system 10 is supported by horizontal support surface 13. The coil 16 is connected through an electrical conductor 22 to scaler power control circuit 20. Control adjuster 21, which may be a variable resistor, is connected through control side 23 to scaler power control circuit 20. Knob 19 is connected to control adjuster 21.

Housing 18 has control side 23, convex side 24, holder side 25, first base side 26 having a having a plurality of first base feet 30, 32, 34 and 36 extending therefrom. Housing 18 has second base side 40 having a plurality of second base feet 42, 44, 46 and 48 extending therefrom. Preferably first base feet 30, 32, 34 and 36 and second base feet 42, 44, 46 and 48 are made of resilient material, such as a polymeric elastomer. Housing 18 has rear side 49. First base side 26 connected to second base side 40 at an angle greater than 30 degrees, and most preferably about 90 degrees. Second base side 40 is connected to holder side 25.

Holder side 25 has a scaler handpiece holder integrally formed therein. First base feet 30, 32, 34 and 36 are adapted to support at least a substantial portion of housing 18. Also, second base feet 42, 44, 46 and 48 are adapted to support at least a substantial portion of housing 18.

First base side 26 is integrally connected to second base side 40, and second base side 40 is integrally connected to holder side 25. Holder side 25 is integrally connected to convex side 24. Control side 23 is integrally connected to both first base side 26 and second base side 40. Also, control side 23 is integrally connected to both holder side 25 and convex side 24.

Holder side 25 has a holder 50 with grips 52, 54 and 56. Grips 52, 54 and 56 are ribs and adapted to retain scaler handpiece 14. When housing 18 is in its vertical position, its horizontal position or in motion between these positions, grips 52, 54 and 56 are adapted to retain scaler handpiece 14 in holder 50. Holder 50 is also adapted to allow the user to readily pull scaler handpiece 14 from holder 50, and to readily push scaler handpiece 14 into holder 50.

Scaler handpiece 14 is connected to handpiece cable 62. Water conduit 60 and handpiece cable 62 extend into housing 18 through rear side 49.

In use system 10 is supported alternatively on first base feet 30, 32, 34 and 36 or on second base feet 42, 44, 46 and 48. While housing 18 is less laterally stable, when supported by first base feet 30, 32, 34 and 36, it requires less horizontal support surface area, than when it is supported by second base feet 42, 44, 46 and 48. Typical horizontal support surface areas used to support system 10 are shelf top, table top and counter top surface areas It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A dental scaler system comprising:
   a dental scaler apparatus and a scaler handpiece having a coil, said dental scaler apparatus having a housing and a scaler power control circuit, said coil being connected through an electrical conductor to said scaler power control circuit,
   said housing being an integrated unit, having a first base side having a plurality of first base feet extending therefrom, a second base side having a plurality of second base feet extending therefrom, and a holder side, said first base side being integrally connected to said second base side at an angle greater than 30 degrees, said second base side being integrally connected to said holder side,
   said holder side having a scaler handpiece holder integrally formed therein, and
   said first base feet being adapted to support at least a substantial portion of said housing, said second base feet being adapted to support at least a substantial portion of said housing.

2. The dental scaler system of claim 1 wherein said housing further comprises a control side, said control side is integrally connected to first base side, said control side is integrally connected to said second base side, and said control side is integrally connected to said holder side.

3. The dental scaler system of claim 1 wherein said holder side has a holder with at least one grip, and said grip is adapted to retain said scaler handpiece.

4. The dental scaler system of claim 3 wherein said grip is a rib.

5. A dental scaler system comprising:

a dental scaler apparatus and a scaler handpiece having a coil, said dental scaler apparatus having a housing and a scaler power control circuit, said coil being connected through an electrical conductor to said scaler power control circuit, said housing being an integrated unit, having a holder side, a first base side having a plurality of first base feet extending therefrom, and a second base side integrally having a plurality of second base feet extending therefrom, said first base side being integrally connected to said second base side at an angle greater than 30 degrees, said second base side being integrally connected to said holder side, said holder side having a holder with at least one grip, said grip being adapted to retain said scaler handpiece, and said first base feet being adapted to support at least a substantial portion of said housing, said second base feet being adapted to support at least a substantial portion of said housing.

6. The dental scaler system of claim 5 wherein said housing further comprises a control side, said control side is integrally connected to first base side, said control side is integrally connected to said second base side, and said control side is integrally connected to said holder side.

7. The dental scaler system of claim 5 wherein said holder has at least two grips, each of said grips extends outwardly from said holder and said holder is adapted to be sufficiently distorted for removal of said scaler handpiece from said holder by the user.

8. The dental scaler system of claim 5 wherein said holder is integrally formed in said holder side.

* * * * *